United States Patent [19]

Hopp et al.

[11] Patent Number: 4,703,004
[45] Date of Patent: Oct. 27, 1987

[54] SYNTHESIS OF PROTEIN WITH AN IDENTIFICATION PEPTIDE

[75] Inventors: Thomas P. Hopp; Susan L. Bektesh; Paul J. Conlon, III; Carl J. March, all of Seattle, Wash.

[73] Assignee: Immunex Corporation, Seattle, Wash.

[21] Appl. No.: 573,825

[22] Filed: Jan. 24, 1984

[51] Int. Cl.[4] .................. C12P 21/00; C12N 1/00; C12N 15/00; C07H 21/04
[52] U.S. Cl. .................. 435/68; 435/172.3; 435/320; 536/27
[58] Field of Search .......... 435/172.3, 68, 317; 536/27-29

[56] References Cited

U.S. PATENT DOCUMENTS

| | | | |
|---|---|---|---|
| 4,366,246 | 12/1982 | Riggs | 435/172.3 |
| 4,468,464 | 8/1984 | Cohen et al. | 435/172.3 |
| 4,503,142 | 3/1985 | Berman et al. | 435/172.3 |
| 4,559,302 | 12/1985 | Ingolia | 536/27 |
| 4,563,424 | 1/1986 | Riggs | 435/172.3 |
| 4,571,421 | 2/1986 | Itakura | 536/27 |

FOREIGN PATENT DOCUMENTS 0035384  9/1981  European Pat. Off. .

Primary Examiner—Blondel Hazel

[57]    ABSTRACT

A hybrid polypeptide composed of an identification peptide and a desired functional protein are produced by recombinant DNA techniques. A DNA expression vector is constructed that includes segments of DNA coding for the identification peptide and the desired functional protein. The identification peptide consists of a highly antigenic N-terminal portion and a C-terminal linking portion that connects the identification peptide to the N-terminal of the functional protein. The linking portion of the identification peptide is cleavable at a specific amino acid residue adjacent the functional protein by use of a sequence specific proteolytic enzyme or chemical proteolytic agent. The hybrid polypeptide expressed by the host cells transformed by the cloning vector is removed therefrom and purified by affinity chromatography techniques by use of an immobilized ligand specific to the antigenic portion of the identification peptide. The protein is then cleaved from the isolated hybrid polypeptide with an appropriate proteolic enzyme or chemical agent, thereby releasing the mature functional protein in highly purified, highly active state.

6 Claims, 2 Drawing Figures

SYNTHESIS OF PROTEIN WITH AN IDENTIFICATION PEPTIDE

TECHNICAL FIELD

The present invention relates to a process for producing protein molecules by recombinant DNA techniques, and more particularly to a process for producing a selected protein by expression of hybrid molecules composed of the selected protein together with an antigenic peptide, purifying the hybrid molecules by an affinity protocol and then cleaving the antigenic peptide from the protein molecule.

BACKGROUND ART

Proteinaceous molecules, such as enzymes, hormones, storage proteins, binding proteins and transport proteins may be produced by recombinant DNA techniques. For instance, DNA fragments coding for a selected protein, together with appropriate DNA sequences for a promoter and ribosome binding site are ligated to a plasmid vector. The plasmid is inserted within a host prokaryotic or eukaryotic cell. Transformed host cells are identified, isolated and then cultivated to cause expression of the proteinaceous molecules.

The desired protein is then isolated from the culture medium and purified by a variety of techniques employed either individually or in combination. These purification procedures may include techniques to segregate the desired protein based on its molecular size. Such procedures include dialysis, density-gradient centrifugation and gel column chromatography. Dialysis and density-gradient centrifugation, however, are not selected enough to highly purify protein. While the use of gel column chromatography results in greater purification, many of the desired protein molecules are lost during the purification process, thereby resulting in a low yield.

Protein molecules also may be separated from mixture by procedures based on solubility differences. For instance, isoelectric precipitation takes advantage of the change in solubility of proteins as a function of pH while solvent fractionation employs the fact that the solubility of proteins vary as a function of the dielectric constant of the medium. Neutral salts, such as ammonium sulfate, are used to precipitate out proteins as a result of decreased protein solubility based on the high ionic strength of the salt. A severe drawback of solvent fractionation is that solvents can cause the proteins to denature. Neither isoelectric precipitation nor salt precipitation are able to purify proteins beyond a moderate level. One advantage of salt precipitation, however, is that it typically gives close to a 100% yield, and thus this method is often employed as an initial step in tandem with other procedures.

Proteins also may be separated based on their ionic properties, for instance, by various types of electrophoresis or by ion-exchange chromatography. Most electrophoresis techniques are used as analytical tools and are not practical on a large scale basis. While ion-exchange chromatography can result in highly purified proteins, the yield level is typically very low, with many of the protein molecules either being lost in prior eluates or remaining bound to the column matrix.

Affinity chromatography often is employed to avoid the negative aspects of the above-mentioned purification procedures including ion-exchange chromatography and gel column chromatography. Affinity chromatography is based on the capacity of proteins to bind specifically and noncovalently with a ligand. Used alone, it can isolate proteins from very complex mixtures with not only a greater degree of purification than possible by sequential ion-exchange and gel column chromatography, but also without significant loss of activity. See Rosenberry et al., "Purification of Acetylcholinesterase by Affinity Chromatography and Determination of Active Site Stoichiometry," 247 *Journal of Biological Chemistry*, 1555-1565 (1972). Although affinity chromatography can produce a high level of protein purification, this technique requires the availability of significant amounts of the corresponding ligand (for instance, antibody for antigen or substrate for enzyme) for the protein molecule being isolated. Thus, it may be necessary to carry out a time-consuming, laborious regime of innoculating mice or other animals with the protein molecule of interest in purified form and then identifying a specific ligand for the protein molecule. Thereafter, the ligand must be amplified, for instance, by hybridoma techniques and then purified for covalent detachment to the affinity column matrix.

It will be appreciated that it may be very difficult to isolate a specific ligand for certain protein molecules. Moreover, specific ligands do not exist for all types of protein molecules, such as certain enzymes. As a consequence, to date, affinity chromatography has not been employed as a universal isolation and purification technique for all protein molecules.

Accordingly, it is a principle object of the present invention to use recombinant DNA techniques for economically producing a desired protein and then efficiently purifying the protein.

It is a specific object of the present invention to provide an affinity purification process wherein a single ligand may be employed to isolate and purify substantially all protein molecules expressed by transformed host cells, whether antigenic or not.

A further particular object of the present invention is to provide a standard, highly efficient process that can be used on a small research level or a large commercial scale to purify substantially all protein molecules produced by recombinant DNA techniques.

An additional particular object of the present invention is to provide technique that is capable of highly purifying substantially any protein molecule generated by recombinant DNA techniques in a single, affinity chromatography step, but without sacrificing high yields.

SUMMARY OF THE INVENTION

In accordance with the present invention, a hybrid molecule composed of a selected or constituent protein and an identification or marker peptide are produced by recombinant DNA techniques. The identification peptide ideally includes two primary components: a highly antigenic N-terminal portion; and, a linking portion to connect the identification peptide to the protein. The linking portion of the identification peptide is characterized by being cleavable at a specific amino acid residue adjacent the protein molecule by use of a sequence specific proteolytic agent. By this particular construction of the identification peptide, the hydrid identification peptide/protein molecules expressed by the transformed host cells can be isolated by affinity chromatography techniques. This is accomplished by constructing an affinity column with immobilized ligands specific to the antigenic portion of the identification peptide thereby to bind the expressed hybrid identification peptide/protein molecule. The bound identification peptide/protein molecules can be liberated from the column and then the identification peptide cleaved from the protein molecule with an appropriate proteolytic agent, thus releasing the desired, highly purified protein molecule.

As a further aspect of the present invention, the antigenic portion of the identification peptide is composed of one or more hydrophilic amino acids and/or amino acids having an aromatic side chain. Both types of amino acids are known to be highly antigenic. The linking portion of the identification peptide is composed of amino acids that are recognized by a sequence specific proteolytic agent which cleaves the linking portion at a location adjacent the protein molecule. Ideally, the amino acid sequence of the linking portion is unique, thus minimizing the possibility that the proteolytic agent will cleave the protein molecule. In accordance with the present invention, the protein molecule may be composed of any proteinaceous substance that can be expressed in transformed host cells.

An additional aspect of the present invention concerns a recombinant cloning vector composed of segments of chemically synthesized DNA coding for the identification peptide. The vector also includes a DNA segment coding for the desired protein molecule. These DNA segments are inserted within a cloning vector, such as a plasmid, by use of appropriate restriction endonucleases and ligases. Ideally, the plasmid has a phenotypic marker gene for identification and isolation of transformed host cells. In addition, the chosen plasmid preferably includes a natural or synthetic promoter for high level expression of the hybrid identification peptide/protein molecule in the host cells. The recombinant plasmid is employed to transform compatible prokaryotic or eukaryotic host cells for replication of the plasmid and expression of the hybrid identification peptide/protein molecule.

The present invention also includes the production of a ligand (antibody) against the antigenic portion of the identification peptide for affinity column purification of the selected protein molecule. Ligands are generated by immunizing mice, rabbits or other appropriate animals with the identification peptide that has been chemically synthesized by well-known techniques. To facilitate antibody production, the synthesized identification peptide can be chemically coupled to a proteinaceous carrier, such as keyhole limpet hemocyanin, bovine or ovine serum albumin or sheep erythrocytes. The substantially larger carrier molecules or cells facilitate recognition of the foreign identification peptide by the immune system of the innoculated animals. As an alternative method to facilitate antibody production, fatty acid derivatized amino acids can be attached to the linking portion of the identification peptide opposite the location of the antigenic portion of the peptide or they can be attached directly to the antigenic portion of the peptide. The fatty acids cause the identification peptide to agglutinate to form micelles, with the fatty acids constituting the center of the micelle with the antigenic portion of the peptide extending outwardly therefrom for optimum presentation to the immune system of innoculated animals. The antibody cells thus produced may be fused to an appropriate myeloma cell to form cell hybrids that generate monoclonal antibodies.

In the affinity purification aspect of the present invention, antibodies produced by the above described procedures are bound to an affinity chromatography column to form an immobolized ligand for the hybrid identification peptide/protein molecules. The hybrid molecules together with growth medium, cell residue, other proteins, etc., are passed over the column. The hybrid molecules which bind to the antibody are eluted from the column by chemical means or by competition from free identification peptide, i.e., without the fatty acid derivatized amino acids attached. The identification peptide is then cleaved from the protein molecule with a proteolytic agent that is specific to the amino acid sequence of the linking portion of the identification peptide. Then, the protein molecule is separated from the identification peptide and the proteolytic agent to release the protein molecule in highly purified form.

It will be appreciated that by virtue of the present invention, only a singular antibody is needed to purify all protein molecules produced by recombinant DNA methods. In addition, the present invention can be used to highly purify all protein molecules produced by recombinant DNA methods, including those that are not susceptible to affinity chromatography procedures.

It is to be understood that some protein products will possess the desired enzymatic or biological activity with the identification peptide still attached thereto. Such identification peptide/protein molecules will be useful in such configuration so that their purification will be complete after elution from the antibody column, without need for the proteolytic cleavage step or subsequent steps.

BRIEF DESCRIPTION OF THE DRAWINGS

The details of typical embodiments of the present invention will be described in connection with accompanying drawings, in which.

DETAILED DESCRIPTION

Figure 1:
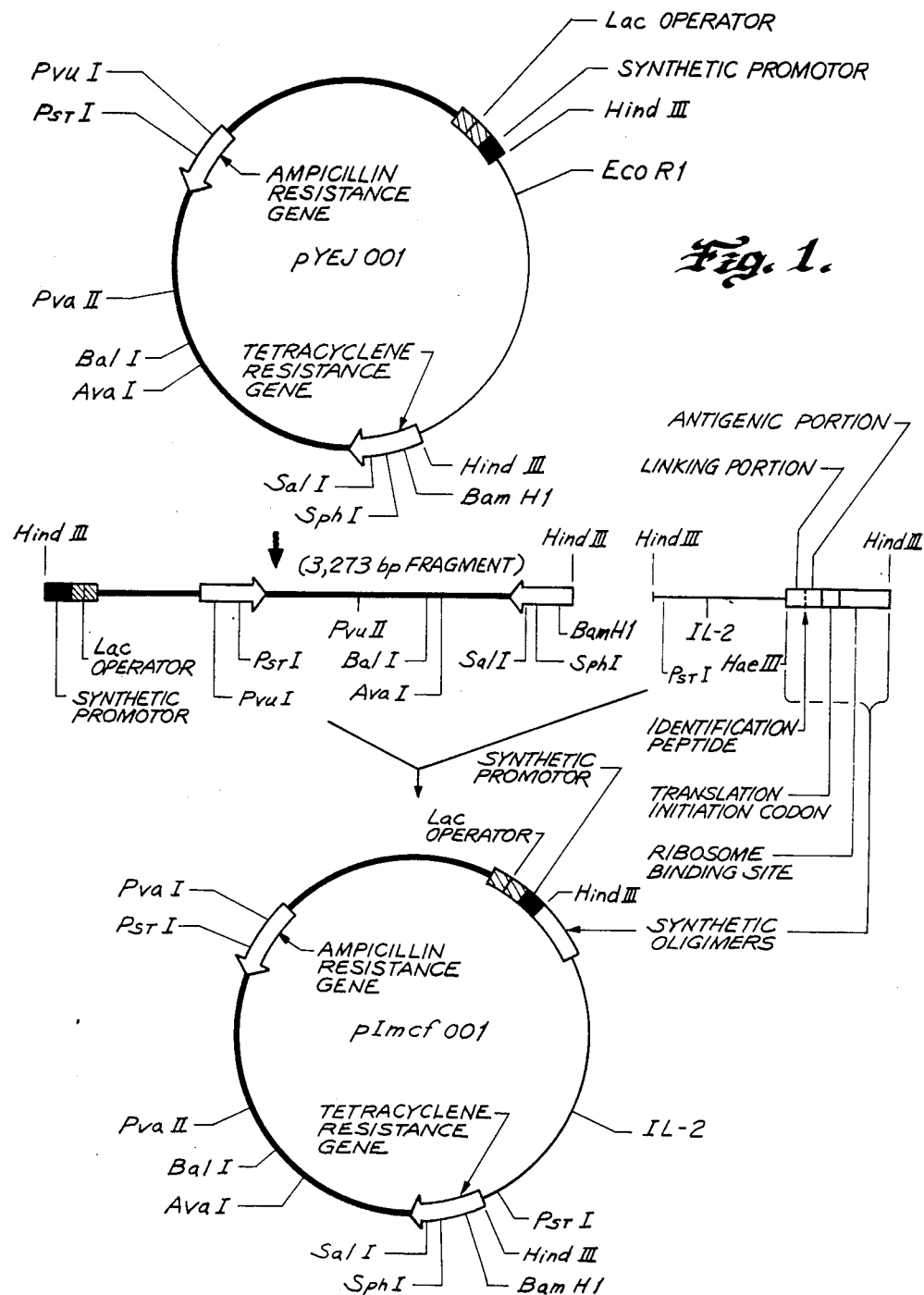
FIG. 1 is a restructuring scheme in preparing plasmid pImcf 001.

In accordance with the present invention, hybrid polypeptide molecules composed of an identification peptide and a desired protein are produced by recombinant DNA techniques and then the hybrid molecules are purified by an affinity chromatography process utilizing a universal ligand. To this end, a DNA expression vector is formed that includes segments of DNA coding for the identification peptide and the desired functional protein. The identification peptide consists of a highly antigenic N-terminal portion and a C-terminal portion that connects the identification peptide to the N-terminus of the protein molecule. The linking portion of the identification peptide is cleavable at a specific amino acid residue adjacent the selected protein molecule by use of a sequence specific proteolytic enzyme or chemical proteolytic agent. The cloning vector is replicated and the hybrid polypeptide is expressed in prokaryotic or eukaryotic cells transformed by the vector. The transformed cells are isolated and then expanded, for instance, in culture or by fermentation process.

Thereafter, the hybrid polypeptide is purified by affinity chromatography. Ligands specific to the antigenic portion of the identification peptide are generated for attachment to a bead column or other type of matrix. An extract of the host cells made from the culture or fermentation is applied to the column and then the polypeptides that bind to the column are eluted. Thereafter, the identification peptide is cleaved from the peptide molecule with an appropriate proteolytic enzyme or chemical agent, thereby releasing the desired mature protein molecule in a highly purified, highly active state.

Identification Peptide

The identification peptide of the present invention is in the form of a linear sequence of amino acids bonded to the N-terminus of the protein of interest. This linear sequence is composed of two basic portions: an antigenic N-terminus or "head" portion; and a linking or "tail" portion to link the identification peptide to the selected protein molecule. As noted above, and as more fully discussed below, the antigenic portion of the identification peptide serves to facilitate isolation and purification of the hybrid polypeptide produced by the transformed host cells. The antigenic portion binds to a specific ligand (antibody) which has been immobilized on a chromatography column or other matrix.

To facilitate the isolation of an antibody against the antigenic portion of the identification peptide for use on the affinity chromatography column, it is desirable that the N-terminus of the identification peptide be highly antigenic. This may be achieved by composing the antigenic portion of one or more hydrophilic amino acids. Such amino acids include Arg, Asp, Glu and Lys. The N-terminus portion of the identification peptide may be composed of a series of several different of these hydrophilic amino acids or simply a chain of the same hydrophilic amino acid.

In addition to, or in place of, the hydrophilic amino acids, amino acids having an aromatic side chain may be employed. These amino acids also are known to be highly antigenic. Such amino acids include Tyr, Phe, His, and Trp. Applicants have found that to optimize the antigenicity of the N-terminus portion of the identification peptide, it is desirable to use both hydrophilic and aromatic amino acids. Also, the number of amino acids composing the antigenic portion is ideally from one to six. However, this number may be increased without departing from the spirit or scope of the present invention.

In accordance with the present invention, the linking portion of the identification peptide serves to connect the identification peptide to the protein of interest. However, once the hybrid polypeptide, composed of the identification peptide and the desired protein, has been purified from the culture extract, the identification peptide is cleaved from the protein. Thus, it is essential that the linking portion of the identification peptide be cleavable at a specific amino acid residue, and ideally at the residue adjacent the N-terminus of the protein molecule. As such, the linking portion is composed of preferably four to six amino acids that are cleavable at a desired residue by a sequence specific proteolytic enzyme or chemical proteolytic agent. However, it is to be understood that the number of residues composing the linking portion may vary from this ideal number without departing from the scope of the present invention.

The linking portion may be composed of a sequence of amino acids ending with either Lys, Arg, Met or Asn proceeded by a series of other different amino acids. This sequence is defined by the equation:

A. $X_{1 \text{ to } n} - R$ where:

$R$ = Lys, Arg, Met or Asn $X_{1 \text{ to } n}$ = a series of any other amino acid(s) except R If Arg or Lys are used as the C-terminus amino acid of the linking portion, then a proteolytic enzyme that cleaves after the Arg or Lys residue can be used to remove the identification peptide from the protein molecule. If Met or Asn are used as the C-terminus amino acid, then an appropriate chemical proteolytic agent that cleaves after these amino acids may be employed to sever the identification peptide from the protein molecule. For instance, cyanogen bromide can be used to cleave after the Met residue.

Although Lys, Arg, Met, or Asn may be employed as a C-terminus amino acid of the linking portion, this may be undesirable if the protein molecule also contains the same amino acid since cleavage of the protein molecule will also be cleaved at these residues. One technique of overcoming this situation is to construct the linking portion from a sequence of amino acids that does not occur commonly in natural form. For instance, one such sequence is composed of: Asp-Asp-Asp-Asp-Lys. The only known natural occurrence of this particular sequence of amino acids is in the protein trypsinogen which is a natural substrate for bovine enterokinase. By utilizing this unique sequence to form the linking portion of the identification polypeptide, the protein molecule can be liberated from the identification peptide by use of bovine enterokinase with very little likelihood that this enzyme will cleave any portion of the protein molecule itself.

It is to be understood that other unique amino acid sequences may also be employed without departing from the spirit or scope of the present invention. For instance, the linking portion can be composed in part of a pair of basic amino acids, i.e., Lys, Arg or His. This sequence is cleaved by kallikreins, a glandular enzyme. Also, the linking portion can be in part composed of Arg-Gly, since it is known that the enzyme thrombine will cleave after the Arg if this residue is followed by Gly.

For a chosen composition of the identification peptide, DNA oligomers coding for the amino acids of the identification peptide may be synthesized using commercially available, automated DNA synthesizer in a manner well known in the art. Because the techniques and apparatus for synthesizing DNA are now common in the art, they need not be set forth here. As discussed below, the synthetic DNA oligomers may be ligated to a DNA sequence coding for the desired protein and then the combined DNA fragments ligated to an appropriate expression vector to form a cloning vehicle for transformation to an appropriate host cell.

Protein Molecule

The present invention may be beneficially employed to produce substantially any prokaryotic or eukaryotic, simple or conjugated, protein that can be expressed by a vector in a transformed host cell. Such proteins include enzymes, whether oxidoreductases, transferases, hydrolases, lyases, isomerases or ligases.

The present invention also contemplates the production of storage proteins, such as ferritin or ovalbumin or transport proteins, such as hemoglobin, serum albumin or ceruloplasmin. Also included are the types of proteins that function in contractile and motile systems, for instance, actin and myosin.

The present invention also contemplates the production of proteins that serve a protective or defense function, such as the blood proteins thrombin and fibrinogen. Other protective proteins include the binding proteins, such as antibodies or immunoglobulins that bind to and thus neutralize antigens.

The protein produced by the present invention also may encompass various hormones such as Human Growth Hormone, somatostatin, prolactin, estrone, progesterone, melanocyte, thryotropin, calcitonin, gonadotropin and insulin. Other such hormones include those that have been identified as being involved in the immune system, such as interleukin 1, interleukin 2, colony stimulating factor, macrophage-activating factor and interferon.

The present invention is also applicable to the production of toxic proteins, such as ricin from castor bean or grossypin from cotton linseed.

Proteins that serve as structural elements may be produced by the present invention; such proteins include the fibrous proteins collagen, elastin and alpha-keratin. Other structural proteins include glycoproteins, virus-proteins and muco-proteins.

In addition to the above-noted naturally occuring proteins, the present invention may be employed to produce synthetic proteins defined generally as any sequence of amino acids not occurring in nature.

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthesized plasmids having genes coding for many different protein molecules are now commercially available from a variety of sources. The desired DNA also can be produced from mRNA by using the enzyme reverse transcriptase. This enzyme permits the synthesis of DNA from an RNA template.

Preparation of DNA Expression Vectors

In accordance with the present invention, once a gene coding for a desired protein molecule is isolated, synthesized or otherwise obtained, it is joined to a synthetic DNA fragment coding for the identification peptide. As noted above, the identification peptide gene may be synthesized by well-known techniques which will not be repeated here. In addition to the protein molecule gene and the identification peptide gene, if needed, the hybrid DNA fragment may include a ribosome binding site for high level protein translation in a host cell, a translation initiation codon (ATG), and a promoter.

The genes coding for the protein molecule and the identification peptide ideally are treated with an appropriate restriction enzyme or are otherwise manipulated to have cohesive termini to facilitate ligation with each other and with a plasmid or other type of cloning vector. The cloning vector is preferably digested with the same restriction endonuclease used to condition the foreign genes to form complementary cohesive termini prior to ligation with the foreign genes. The resulting cloning vector is used to transform a host microorganism. The transformants are isolated and analyzed for the presence of the foreign genes and for the proper orientation of the genes within the vector. The transformants are then multiplied in culture to cause replication of the vector and high level expression of the hybrid polypeptide being sought. In addition, the cloning vectors may be used to transform other strains of the chosen host or other types of hosts for large scale production of the hybrid heterologous polypeptide. Various procedures and materials for preparing recombinant vectors, transforming host cells with the vectors, replicating the vector and expressing polypeptides and proteins are discussed by Old and Primrose, *Principals of Gene Manipulation*, (2d Ed. 1981), which disclosure is incorporated herein by reference.

To carry out the present invention, various cloning vectors may be utilized. Although the preference is for a plasmid, the vector may be a bacteriophage or cosmid. If cloning takes place in mammalian or plant cells, viruses can be used as vectors. If a plasmid is employed, it may be obtained from a natural source or artificially synthesized. The particular plasmid chosen should be compatible with the particular cells serving as the host, whether a bacteria such as *Escherichia coli* (*E. coli*), yeast, or other unicellular microorganism. The plasmid should have the proper origin of replication (replicon) for the particular host cell chosen. In addition, the size of the plasmid must be sufficient to accommodate the hybrid genes coding for both the protein molecule of interest and the identification peptide, but also of as low a molecular weight as possible. Low molecular weight plasmids are more resistant to damage from shearing and are more readily isolated from host cells. If obtained from natural sources, they are usually present as multiple copies, thereby facilitating their isolation. Also, there is less likelihood that a low molecular weight plasmid has multiple substrate sites for restriction endonucleases.

Another requirement for a plasmid cloning vector is the existence of restriction enzymes to cleave the plasmid for subsequent ligation with the foreign genes without causing inactivation of the replicon while providing suitable ligatable termini that are complementary to the termini of the foreign genes being inserted. To this end, it would be helpful for the plasmid to have single substrate sites for a large number of restriction endonucleases.

Moreover, the plasmid should have a phenotypic property that will enable the transformed host cells to be readily identified and separated from cells which do not undergo transformation. Such phenotypic selection genes can include genes providing resistance to a growth inhibiting substance, such as an antibiotic. Plasmids are now widely available that include genes resistant to various antibiotics, such as tetracycline, streptomycin, sulfa drugs, penicillin, and ampicillin. When host cells are grown in a medium containing one of these antibiotics, only transformants having the appropriate antibiotic resistant gene will survive.

Rather than utilizing a gene resistant to a growth inhibiting compound to identify transformed host cells, phenotypic selection genes can also include those that provide growth factor to permit transformed cells to propagate in a medium which lacks the necessary growth factor for the host cells. For instance, for yeast auxotrophs, such growth factors include tryptophan or leucine.

If *E. coli* is employed as the host cell, a preferred plasmid for performing the present invention is pYEJ001 (PL Biochemicals). This plasmid has genes coding for both ampicillin and tetracycline resistance. It also includes an origin of replication for propagation in *E. coli* and has both a lac operon and synthetic promoter sites for high level expression of foreign genes in *E. coli*.

A partial restriction endonuclease cleavage map of this plasmid is shown in FIG. 1.

An alternative plasmid for high level expression in *E. coli* is pBR322. This plasmid was constructed and described by Bolivar et al., 2 *Gene* 95-113 (1977) and has been highly characterized and fully sequenced by Sutcliffe, 43 *Cold Spring Harb. Symp. Quant. Biol.,* (1) 77-90 (1979).

Figure 2:
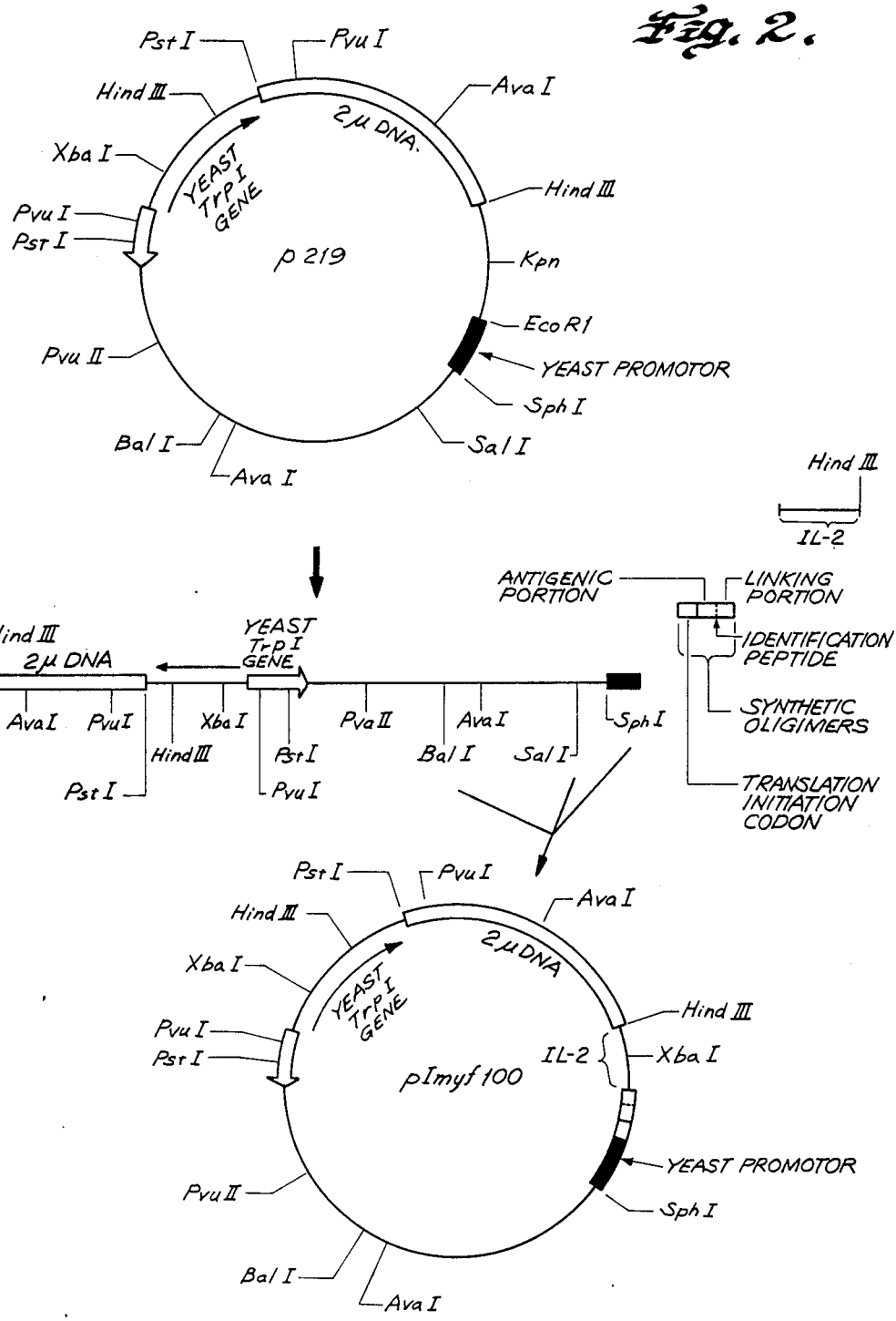
FIG. 2 is a restructuring scheme in preparing plasmid pImyf 100.

If yeast cells are employed as transformants, p219 is a preferable plasmid. Samples of this plasmid are on deposit with the American Type Culture Collection (ATCC), 12361 Parklawn Drive, Rockville, Md. 20852, under accession number 39550. As shown in FIG. 2, this plasmid has a yeast promoter sequence for propagation of the plasmid in both yeast and *E. coli*. In addition, it has a selectable marker, ampicillin resistant gene, for selection of the plasmid in *E. coli* and the yeast trp 1 gene for selection in yeast trp-auxotrophs.

If a bacteriophage is used instead of a plasmid, such phages should have substantially the same characteristics used to select a plasmid as discussed above. This includes the existence of a phenotypic marker gene and ligatable termini for attachment to foreign hybrid genes coding for the identification peptide and the protein molecule of interest.

To prepare the chosen plasmid for ligation, preferably, it is digested with a restriction endonuclease to produce a linear segment(s) in which the two DNA strands are cleaved at closely adjacent sites to produce cohesive termini ("sticky ends") bearing 5'-phosphate and 3'-hydroxyl groups, thereby facilitating ligation with the foreign genes. For the plasmids identified above, the restriction endonucleases Hind III and Eco RI will produce this result. As identified in the cleavage maps shown in FIGS. 1 and 2, other restriction endonucleases may be employed to cleave the plasmids at other target sites. Also, the plasmid may be sequentially treated with two different restriction endonucleases to produce dissimilar termini configurations to facilitate ligation of foreign DNA fragment(s) in the proper orientation.

Certain restriction enzymes (Pvu II, Bal I) may result in the formation of square or blunt ends. The square ends of the plasmid can be joined to the foreign genes with an appropriate ligase. Alternatively, nucleic acids can be added to the 5' and or 3' ends to form cohesive termini, for instance, by use of linkor molecules. Instead, bases may be removed from the flush ends with appropriate enzymes to form cohesive termini. The methods and materials for achieving this are well known in the art. See *Old and Primrose,* supra.

Ideally, the linearized plasmid vector is treated with an alkaline phosphatase to remove the 5'-terminal phosphate groups. This will prevent recircularization of the plasmid; it will leave one nick at each end of the foreign DNA remaining unligated from the plasmid. However, after transformation of a host organism, cellular repair mechanisms will repair the nick.

It is to be appreciated that digestion of the chosen plasmid with a restriction endonuclease(s) may result in the formation of two or more linear DNA segments. The segment to be used to form the cloning vector, i.e., the segment having the phenotypic identity gene, replicon and other desired components, may be identified by well-known techniques, such as by gel electrophoresis.

Prior to being joined with the selected cloning vector, it is desirable that the foreign genes coding for the identification peptide and the selected protein are first joined together. Ideally, the gene coding for the protein molecule is treated with the same restriction endonuclease used to cleave the plasmid vector so that the appropriate terminus of the gene will be compatible with the corresponding terminus of the plasmid. This gene also may be treated with a second, different restriction endonuclease to prepare its opposite terminus for ligation with the identification peptide gene.

Since the gene coding for the identification peptide is formed by chemical synthesis, it can be constructed with appropriate termini configurations to facilitate ligation to the protein molecule gene and the corresponding terminus of the plasmid. Oligomers coding for the ribosome binding site and a translation initiation codon (ATG) may also be synthesized. The synthetic DNA oligomers for the identification peptide, ribosome binding site and translation initiation codon are joined to the protein molecule gene in vitro with an appropriate DNA ligase, by established techniques.

In the ligation reaction, adenosinetriphosphate (ATP), nicotinamide-adenine dinucleotide (NAD+) or other appropriate cofactors are used with the DNA ligase. In addition, dithiothreitol may be added as a reducing agent and spermidine added as a DNA stabilizer. Also, a protein source, such as bovine serum albumin (BSA) can be employed to prevent denaturization. Ideally, the molar ratio of the genes coding for the protein molecule and the synthetic oligomers are in the range of about 1-5:5-1. After ligation the resulting DNA strands are analyzed, for instance, by gel electrophoresis, to identify whether those composed of segments of DNA coding for the protein molecule are properly cointegrated with the synthetic oligomers.

The cointegrate genes are next ligated to the linearized plasmid fragment in a solution containing a ligase buffer and an appropriate DNA ligase. Preferably, the molar ratio of plasmids to the cointegrate genes is in the range of about 1-5:5-1. As in the ligation of the protein molecule gene to the identification peptide gene, discussed above, this ligation protocol also requires a coenzyme such as ATP or NAD+ and preferably utilizes a protein source, reducing agent and DNA stabilizer. After incubation, the recircularized plasmid having the current orientation of the cointegrate genes are identified by standard techniques, such as by gel electrophoresis.

Transformation of Recombinant DNA Plasmid

The recombinant DNA plasmids, as prepared above, are used for the transformation of host cells. Although the host cell may be any appropriate prokaryotic or eukaryotic cell, preferably it is a well-defined bacteria, such as *E. coli* or a yeast strain. Both such hosts are readily transformed and capable of rapid growth in fermentation cultures. In place of *E. coli,* other unicellular microorganisms can be employed, for instance fungi and algae. In addition, other forms of bacteria such as salmonella or pneumococcus may be substituted for *E. coli*. Whatever host is chosen, it should be one that does not contain a restriction enzyme that would cleave the recombinant plasmid and that has the necessary biochemical pathways for phenotypic expression and other functions for proper expression of the hybrid polypeptide.

If *E. coli* is chosen, preferable strains include RR 1 and HB 101, both of which are widely available. For transformation in yeast, preferable strains include DB 746 and DBK 747. These strains also are widely available (for instance, from the ATCC as strain Nos. 44 773 and 44 774, respectively).

The techniques for transforming recombinant plasmids in *E. coli* strains are widely known. A typical protocol is set forth in U.S. Pat. No. 4,332,900. Procedures for transforming yeast cells with recombinant plsmids are also known. See Beggs, 275 *Nature* 104–109 (1978).

In transformation protocols, only a small portion of the host cells are actually transformed, due to limited plasmid uptake by the cells. Thus, before transformants are isolated, the host cells used in the transformation protocol typically are multiplied in an appropriate medium. The cells that actually have been transformed can be identified by placing the original culture on agar plates containing a suitable growth medium containing the phenotypic identifier, such as an antibiotic. Only those cells that have the proper resistant gene will survive. Cells from the colonies that survive can be lysed and then the plasmid isolated from the lysate. The plasmid thus isolated can be characterized inter alia to determine if the cointegrate genes are ligated in the correct orientation, by digestion with restriction endonucleases and subsequent gel electrophoresis or by other standard methods.

Once transformed cells are identified, they can be multiplied by established techniques, such as by fermentation. In addition, the recovered cloned recombinant plasmids can be used to transform other strains of bacteria or other types of host cells for high scale replication and expression of the hybrid polypeptide.

Purification of Hybrid Polypeptide

The hybrid polypeptide molecules expressed by the transformed host cells are separated from the culture medium, other cellular material, etc. preferably by an affinity chromatography process. To this end, antibodies against the identification peptide portion of the hybrid polypeptide must be generated for use on a column matrix. To produce such antibodies, the identification peptide is first synthesized and then used to immunize an appropriate animal for production of an antibody against the identification peptide. The antibody can be identified by an enzyme-linked immunosorbent assay (ELISA) or other appropriate assay. A monoclonal then can be produced by hybridoma techniques. After purification, this antibody is bound to the column matrix and then an extract from the transformed host cells applied to the column to isolate the hybrid polypeptide. The hybrid polypeptide is eluted from the column, for instance, by competition from free identification peptide. The identification peptide is cleaved from the protein molecule and then the protein molecule is separated from the identification peptide, thereby resulting in a purified protein.

Synthesis of Identification Peptides

The identification peptide is chemically synthesized in various configurations, one for use in generating antibodies against the peptide and another for use as a competitor to liberate the hybrid polypeptides from the affinity column. In both of these configurations, the synthesized identification peptide includes amino acid residues forming an antigenic N-terminal portion that is bonded to adjacent residues forming a linking portion of the peptide. The particular amino acid residues employed in these two portions of the identification polypeptide were detailed above.

In the form of the identification peptide employed to generate antibodies, additional amino acids that are derivatized with a fatty acid may be added to the end of the linking portion of the peptide opposite the antigenic N-terminal portion so that the identification peptides form micelles in an aqueous solution. The fatty acid molecules that are hydrophobic constitute the center of the micelle, with the antigenic N-terminal portion of the identification peptide radiating outwardly from the center of the spherical micelle. Applicants have found that the formation of such micelles result in an optimal method for presenting the identification peptide to the immune system of an animal.

In a preferred form of the present invention, a number of spacer amino acids are interposed between the linking portion of the identification peptide and the fatty acid derivatized amino acids to enable the antigenic portion of the identification peptide to extend radially outwardly from the center of the micelle. As such, ideally, the spacer amino acids should be neutral, neither hydrophilic or hydrophobic. The fatty acid derivatized identification peptide of the present invention can be represented by the formula:

$$R_1-R_2-R_3-R_4 \atop | \atop FA \qquad \text{B.}$$

wherein:

$R_1$ = from 1 to 6 hydrophilic amino acids (Arg, Asp, Glu, Lys) and/or amino acids having an aromatic side chain (Tyr, Phe, His, and Trp).

$R_2$ = from 4 to 6 linking amino acids that are cleavable at a specific residue by a sequence specific proteolytic enzyme or chemical proteolytic agent.

$R_3$ = from 1 to 6 spacer amino acids selected from the group Gly, Pro, or Ser.

$R_4$ = from 1 to 3 acids selected from the group consisting of Lys or Ornithine.

FA = a fatty acid.

The compositions of the $R_1$ and $R_2$ amino acids are discussed above. The spacer amino acids, $R_3$, are ideally composed of from one to six uncharged amino acids Gly, Pro or Ser. However, this number may vary without departing from the spirit or scope of the present invention. By being neutral, the spacer amino acids form an uncharged link between the $R_1$ and $R_2$ amino acid residues and the derivatized amino acid residues, thereby avoiding any attraction or repulsion between the individual peptides to enable them to extend radially outwardly in substantially linear configuration from the center of the micelle without interfering with each other.

The $R_4$ amino acid residues are ideally composed of from 1 to 3 diamino acids, such as Lys, or a nonprotein amino acid, such as ornithine. Other diamino acids also may be employed. Also, the actual number of residues employed may be increased from this ideal number without departing from the scope of the present invention.

Substantially any fatty acid may be used that causes the formation of micelles when subjected to water. Applicants have found that palmitic, oleic or stearic acids exhibit this characteristic.

The derivatized identification polypeptide may be chemically synthesized by established techniques. Of preference is the solid phase technique developed by R. B. Merrified which permits the peptide to be built residue by residue from the carboxyl terminal amino acid to the amino terminal amino acid either manually or with an automated, commercially available synthesizer.

The synthesis technique employs widely available solid resin particles, for instance beads, that are large enough to be separated from liquid phase by filtration. Such particles are available with an initial amino acid, such as Gly, already attached to them. Moreover, the initial amino acid is typically provided as a N-alpha-butyloxycarbonyl (N-alpha-BOC) derivative, with both its end and side chains protected. This protected initial amino acid is prepared for attachment to a $R_4$ diamino acid by treating the residue with a dilute acid to remove the N-alpha-BOC group). Deprotection is confirmed by conducting a standard ninhydrin test on a small sample of the resin. If the resin has not been deprotected, the above procedure is repeated, however, if the resin has been deprotected, the amino acid is neutralized with a hindered base and then is ready for reaction with a first diamino acid.

The diamino acid, R4, used is differentially protected, for instance, in the form of N-alpha-tertiary butyloxycarbonyl-epsilon-fluorenylmethyloxycarbonyl (N-alpha-BOC-FMOC) derivative. This particular derivative allows the selected deprotection of the epsilon amino group for coupling of the diamino acid to a fatty acid or other lipophilic, micelle forming substance. Thereafter, the alpha-BOC group is removed by the usual acid treatment and the next amino acid residue added. To couple the diamino acid to the residue, it is activated with a carbodiimide condensing agent and is mixed with the resin. Thereafter, a ninhydrin test conducted to ascertain whether coupling has taken place. If so, the diamino acid residue is ready for the addition of a fatty acid to its side chain. If coupling does not occur the above procedure is repeated. The resin is now ready for the addition of the fatty acid to the diamino acid.

The diamino acid ($R_4$) is derivatized with a fatty acid, FA, by essentially repeating the above-described procedure for coupling the diamino acid to the initial amino acid covalently bound to the resin matrix. A base, such as piperidine, is used to deprotect the epsilon amino group.

The above-described procedures for bonding the diamino acid to the N-terminus of the prior residue and bonding of the fatty acid to the epsilon amino group of the diamino acid are repeated until the desired number of derivatized amino acids are attached to the residue chain. Then the remainder of the amino acid residues composing the spacer residues ($R_3$), the linking residues ($R_2$), and the antigenic residues ($R_1$), are added to the resin using the procedure set forth above; of course, with the appropriate amino acid substituted for the diamino acid ($R_4$) used above.

After the last residue of the antigenic portion of the peptide is coupled to the resin, its N-terminus is deprotected with a dilute acid. Thereafter, side blocking groups of the residues are deprotected and the peptide cleaved from the resin by a standard acid treatment. Lastly, the peptide is isolated from the resin.

The identification peptide described above can be constructed without the linking residues. Instead, the antigenic residues prepared by the above methods, can be coupled directly to the spacer residues without seriously compromising the ability of the peptide to raise antibodies in the animal immunized with the peptide. This form of the identification peptide can be represented by the formula:

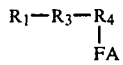
C.

where $R_1$, $R_3$, $R_4$ and FA are as described in conjunction with formula B above.

As another alternative construction, the $R_1$ portion of the identification peptide by itself or together with the $R_2$ residues can be chemically coupled to substantially larger carrier protein molecules or cells by well-known techniques. The carrier molecules/cells help facilitate detection of the identification peptide by the immune system of the animal that is immunized. Such protein molecules include, for instance, keyhole limpet hemocyanin, sheep erythrocytes or bovine or ovine serum albumin.

A second general form of the synthesized identification peptide is used as a competitor molecule in the affinity chromatography procedure. This liberates the hybrid polypeptide from an antibody affinity column, as discussed more fully below. As such, the peptide is synthesized in "free" forms, i.e., without the derivatized diamino acids ($R_4$) or spacer residues ($R_3$) or without the $R_4$, $R_3$ or $R_2$ residues. Except for this difference, the "free" forms of the identification peptide are prepared with the same procedure used to prepare the derivatized identification peptide.

Although the identification peptides have been described as being chemically synthesized with a solid phase resin, the synthesis procedure can be performed entirely in solution without the resin. In this case, the reactions and the final products are essentially identical to those described above.

Generation of Polyclonal Antibody Against the Antigenic N-Terminus of the Fatty Acid Derivatized Identification Peptide The chemically synthesized, fatty acid derivatized identification peptide is utilized to generate a polyclonal antibody against the peptide for use in affinity purification of the hybrid identification peptide/protein molecules expressed by use of the recombinant DNA techniques discussed above. The polyclonal antibody is generated in animals, for instance rabbits, by standard, well-known techniques. In summary, young rabbits are immunized subcutaneously and intradermally in the back with the fatty acid derivatized identification peptide. The immunization is conducted periodically, and in various amounts to induce in vivo generation of an antibody directed against derivatized identification peptide. Ideally the immunizations are conducted weekly with the initial immunization in a 100–500 microgram dose and the remaining immunizations in 100 microgram doses. Rather than utilizing the derivatized identification peptide singularly, it may be mixed with complete or incomplete Freund's adjuvant. Ideally complete Freund's adjuvant is used in the initial immunization while the derivatized identification peptide is emulsified in incomplete Freund's adjuvant for the remaining immunizations. Also, rather than injecting the entire volume of derivatized identification peptide in one body location, preferably on each occasion multiple injections are placed subcutaneously and intradermally in the back of the rabbits.

Immediately prior to the fourth immunization, the rabbits are bled and serum samples tested for anti-identification peptide responses in an ELISA assay. When the rabbit serum titer is high enough to react with the identification peptide at dilutions of 1:1000 or greater, the rabbits are bled and then the serum prepared, after allowing the blood to clot by high speed centrifugation. The immunoglobin G (IgG) fraction from the serum is then purified by standard techniques, such as by Protein A affinity chromatography or by use of an immobilized peptide column. The purified IgG fraction can be used as one source of antibody for affinity purification of the hybrid identification peptide/protein molecules.

Preparation of Monoclonal Antibodies Against the Derivatized Identification Peptide The chemically synthesized, fatty acid derivatized identification peptide is also employed to generate monoclonal anti-identification peptide antibodies for use in the affinity chromatography procedure employed to purify the identification peptide/protein molecules. The preferred procedure for generating the monoclonal anti-identification peptide antibodies is essentially as disclosed in U.S. Pat. No. 4,411,993, incorporated herein by reference. In the procedure, BALB/c mice are immunized with the chemically synthesized, fatty acid derivatized identification peptide on several occasions at intervals of from 7 to 14 days. Various amounts of identification peptide are employed in each injection, ideally from 10 to 100 micrograms. In the initial injection, the identification peptide ideally is emulsified with complete Freund's adjuvant and in the subsequent inoculations, the identification peptide is emulsified and incomplete Freund's adjuvant. Rather than injecting the entire volume of identification peptide in one body location, on each occasion multiple injections are placed about the body of the mice, for instance, in the hind legs.

During the course of immunization, serum samples from the mice are tested by an ELISA assay for an anti-identification peptide response. Once an antibody titer is detected, the animals are given an intravenous injection of the identification peptide mixed with saline. Several days later the animals are sacrificed and their spleens harvested. Single cell suspensions from the splenocytes are cultured in tissue culture medium supplemented with various additives to expand the number of antibody producing cells. The antibody producing cells are isolated from the culture and purified by standard techniques for subsequent fusion with myeloma cells.

In the fusion process, the purified antibody producing spleen cells are mixed with murine myeloma cells and then the mixture pelleted. Thereafter, a fusing agent is added to the cell pellet to facilitate fusion of the two different types of cells by centrifugation. Fusing agents may include various types of condensation polymers of ethylene oxide and water, such as polyethylene glycol (hereinafter "PEG") 1500. Other possible fusing agents include DNA transforming viruses, such as Sendai virus or the fusion protein obtained therefrom. For optimum fusion, the quantity and concentration of the fusing agent must be controlled. For instance, if PEG 1500 is used, this fusing agent should comprise about 40% (weight/volume). However, the volume PEG 1500 may range from 0.5 to 3 milliliters (ml) and the concentration of PEG 1500 may vary from 35% to 60% weight/volume of culture medium.

The cells are then resuspended in a tissue culture medium supplemented with various additives, and selected suppressing agents to preclude the growth of unfused myeloma cells, double myeloma hybrids, unfused spleen cells and double spleen cell hybrids thereby liberating the anti-identification peptide antibody producing monoclonal cells. Such growth inhibitors or suppressants may include hypoxanthine, aminopterin and thymidine (hereinafter collectively referred to as "HAT").

Filler cells are also added to the tissue culture medium to induce proliferation of the hybrid antibody producing cells. Although not yet definitely confirmed, it is considered that the filler cells function to provide optimum cell density to allow small numbers of hybrid cells to multiply more readily. Also, it is thought that the filler cells may provide the hybrid cells with nutrients required for their proliferation. Various types of filler cells may be employed, including thymocytes from the BALB/c mouse. Other types of filler cells include murine spleen cells, irridated murine peritonal exudate cells and murine macrophages. Although various concentrations of filler cells may be added to the culture medium, preferably the filler cells should be added to the HAT containing cultures in concentrations ranging from 0.5 to $5 \times 10^6$ cells per ml with an optimum density of about $3 \times 10^6$ cells per ml.

Rather than being grown as a single culture, the resuspended cells together with the growth medium, filler cells and selected suppressing agents are plated in multiple microtiter plates. After several days of culture, the hybridoma cells which are generated by this procedure are screened by ELISA assay for anti-identification peptide antibody responses.

The hybrid cells which give positive ELISA results are harvested and cloned by a limiting dilution technique, as detailed in U.S. Pat. No. 4,411,993. In the limiting dilution procedure, anti-identification peptide antibody producing hybrid cells are individually cultured in vitro in medium containing filler cells and selected suppressing agents which prevent the growth of unfused spleen and myeloma cells. The cloning cultures which give rise to hybrid cell growth are screened by ELISA assay for reactivity against the identification peptide.

The cloned hybridomas which produce antibody containing supernates reactive with the identification peptide are harvested and then cultured in vitro in larger volumes for bulk production. Alternatively, the anti-identification peptide antibody may be expanded in vivo by injecting the cloned hybridoma cells into the peritoneal cavity of mice and thereafter collecting the interperitoneal ascites which contain high concentrations of anti-identification peptide antibody. Applicants have found that the ascites fluid collected contains monoclonal anti-identification antibody at concentrations in excess of 3 mg per ml. The antibodies contained in the ascites fluid can be isolated and concentrated by established techniques, such as by differentiation ammonium sulfate precipitation followed by gel column chromatography. If required, the antibody can be further purified by ion exchange chromatography and/or affinity chromatography based on the ability of the antibody to bind to protein A from *Staphylococcus aureas* and/or affinity chromatography on an immobilized identification peptide column.

ELISA Assay

As noted above, the polyclonal antibody, hybridoma supernates and monoclonal antibodies were tested for anti-identification peptide responses in an ELISA assay as described by Engvall et al. in "Enzyme-linked immunosorbent assay (ELISA): quantitative assay for immunoglobulin," 8 *Immunochemistry* 871–874 (1971).

Since this type of assay is well known it will only be briefly outlined here.

Chemically synthesized identification peptide is diluted to a concentration of approximately 1 microgram (ug) per milliliter in phosphate buffered saline (PBS). Approximately 25 microliters (ul) of this solution is placed in replicate microliter plate wells. The fluid from the solution is allowed to evaporate during an incubation process thereby to non-specifically adhere the synthetic peptide to the plastic well walls. After each well is washed with approximately 100 ul of PBS, additional PBS containing 1% BSA (by weight) is added to each well and then the plate incubated at 37° C. for an additional hour to block all of the remaining sites on the bottom of the plastic well that have not already bound the identification peptide. The BSA thereby prevents non-specific adherence of the antibody of interest to the wells. After this additional incubation, the PBS solution is decanted.

Next, samples to be tested (animal serum containing polyclonal antibodies, monoclonal antibodies or hybridoma supernates) are added to the wells and incubated for approximately 90 minutes at 37° C. After incubation, the antibody solutions are removed and each well repeatedly washed with PBS or by rinsing with tap water. Thereafter, approximately 50 ul of an enzyme-labeled anti-immunoglobulin antibody is added to each well, for instance, an alkaline phosphatase conjugated secondary antibody. If the assay is being employed to detect hybridoma supernates with anti-identification peptide reactivity, the alkaline phosphatase conjugated reagent is a goat anti-mouse IgG antibody (Sigma Chemical Co., St. Louis, MO) used at a 1:700 dilution in PBS containing approximately 1% BSA. If the assay is being employed to detect polyclonal antibodies to the identification peptide, for instance from rabbit sources, the alkaline phosphatase conjugated reagent is a goat anti-rabbit IgG antibody (Sigma Chemical Co., St. Louis, MO) used at approximately 1:200 dilution in PBS containing approximately 1% BSA.

After reactions with the appropriate alkaline phosphatase coupled antibody, each well is repeatedly washed with either normal saline (approximately 0.9% weight/volume) or by immersion in tap water. Next, approximately 100 ul of a colorless alkaline phosphatase substrate is then added to each well. One such substrate is paranitrophenyl phosphate (Sigma Chemical Co., St. Louis, MO). This substrate is prepared at a strength approximately 1 mg/ml together with approximately 0.1M glycine (pH 10.4), 1 mM zinc chloride, and 1 mM magnesium chloride. If the anti-identification peptide antibody has bound to the identification peptide coated to the plate, a colored product is formed. The optical density of the color can be ascertained by measuring the abortion at the proper wavelength for the particular color. The value of the optical density measured is directly proportional to the quantity of anti-identification peptide antibody in the well sample.

Affinity Purification of Hybrid Identification Peptide/Protein Molecules

Polyclonal or monoclonal antibodies with particularly low affinities for the identification peptide are selected for use to purify the hybrid identification peptide protein molecules. These antibodies are identified by the ability of the free identification peptide or moderate concentrations of salts (for example, 1M NaCl) to inhibit binding of the antibodies to the identification peptide coated microtiter plate wells in the ELISA assays (see above) or by elution from an identification peptide affinity column with a moderate concentration of salt. Antibodies with lower affinities for the identification peptide are more useful for column elution purposes in that they permit release of the identification peptide without having to use harsh eluting agents that can detrimentally damage the peptide.

The low affinity anti-identification peptide antibody, identified and purified as in the manner set forth above, is coupled to a column gel. The unreacted sites of the gel are then blocked by use of a blocking agent, such as glycine ethyl ester. The antibody-coupled gel is washed extensively with a buffer such as borate buffered saline (BBS) or phosphate buffered saline (PBS). Next, the hybrid identification peptide protein molecules are applied to the column and then the column rewashed with buffer. Th hybrid identification peptide protein molecules are specifically eluted from the column by competition with a high molar concentration free identification peptide or moderate concentrations of salts, e.g., 1M NaCl. The free identification peptide substantially out competes the hybrid identification peptide/protein molecules for the antibody coupled to the gel, whereas the 1M NaCl disrupts ionic interactions between the antibody and the identification peptide/protein molecule. As a result, a high yield of highly purified hybrid, identification peptide protein molecules is obtained.

Separation of Mature Protein From Purified, Hybrid Identification Peptide/Protein Molecules The hybrid molecules purified by the above discussed affinity chromatography procedure are now ready for cleavage of the identification peptide from the mature protein molecule. This is accomplished by first suspending the hybrid identification peptide/protein molecules in buffer. Thereafter, the proteolytic enzyme or other chemical proteolytic agent that is specific for the amino acid residues composing the linking portion of the identification peptide is added to the suspension. The enzyme may be coupled to a gel matrix to prevent contamination of the product solution with the enzyme. As discussed above, the proteolytic enzyme or chemical proteolytic agent cleaves the hybrid polypeptide between the adjacent amino acid residues of the linking portion of the identification polypeptide and the protein molecule. As also noted above, as a nonlimiting example, the linking amino acids may be composed of the sequence: Asp-Asp-Asp-Asp-Lys. This particular sequence of amino acids is only known to occur naturally in the protein trypsinogen, the substrate for bovine mucosal enterokinase. Thus, by use of this particular amino acid sequence it is highly unlikely that enzyme cleavage of the hybrid identification peptide protein molecules would also cause cleavage of the protein molecule itself.

After incubation, the desired protein is purified as follows. If the proteolytic agent is an enzyme attached to a gel matrix, the suspension is centrifuged and the pellet (containing the enzyme-gel conjugate) is discarded. The supernatant contains only the protein product, the cleaved identification peptide and possibly small amounts of uncleaved peptide/protein molecule, in addition to buffer salts. In the case of chemical cleavage agents, there would be no gel centrifugation step, and the solution would contain a residual chemical agent and by-products of the chemical agent in addition to the protein product, identification peptide and small amounts of uncleaved peptide/protein molecule.

Most of the above-mentioned contaminating substances are much smaller than the protein product and can be efficiently removed by simple means, such as gel filtration or dialysis. Only the uncleaved identification peptide/protein molecule would remain to contaminate the protein product after such steps. To remove the peptide/protein molecule from the protein product, the mixture is passed over a second affinity column, which column has attached to it the ame antibody specific for the identification peptide as was used for removal of the peptide/protein molecule from the original production medium. The antibody binds the unwanted peptide/protein molecule, and the eluate from the column contains only the desired product protein, now free of all contaminants.

If a soluble enzyme is used for proteolytic cleavage, then the protein product may contain small amounts of the enzyme, which can be removed by passing the solution over an affinity column containing an immobilized substrate for the enzyme. The enzyme is thereby bound to the column and the desired protein molecules allowed to pass through.

As noted above, some protein products will possess the desired enzymadic activity with the identification peptide still attached thereto. As a consequence, the identification peptide need not be cleaved from the protein molecule, thus the above described cleave and subsequent purification steps need not be performed.

Moreover, in situations in which the identification peptide remains attached to the protein molecule, the linking portion of the identification peptide is not needed. Instead, the identification peptide can be composed solely of the antigenic residues. In this situation the construction and method of preparing the DNA expression vectors, detailed above, can be appropriately modified.

EXAMPLE 1

Preparation of Recombinant Plasmid for *E. coli* Host Cell Transformation

Four separate DNA oligomers, as shown in Table 1, are chemically synthesized as described by, for instance: (1) Letsinger et al., 97 *Journal of American Chemical Society*, 3278 (1975); (2) Matteucci et al., 21 *Tetrahedron Lett.*, 719 (1980); and (3) Matteucci et al, 103 *Journal of American Chemical Society*, 3185 (1981).

tion peptide. As shown in Table 1, when the four synthetic oligomers are combined, they define a terminus compatible with a Hind III restriction endonuclease cleavage site. The other terminus of the synthetic fragment coincidentally corresponds to a Hae III restriction endonuclease cleavage site.

DNA coding for the selected protein, Interleukin 2 (IL-2), a regulatory hormone of the human immune system, for expression in transformed host cells, is prepared according to the procedures disclosed by Taniguchi et al., "Structure and Expression of a Cloned cDNA for human Interleukin 2," 302 *Nature* 305 (Mar. 24, 1983). The beginning terminus of the IL-2 DNA fragment is treated with linker molecules or by other appropriate method to form a blunt end corresponding to a T4-DNA polymerase cleavage site. The opposite end of the DNA fragment is appropriately treated to be compatible with Hind III cleavage site. The DNA coding for IL-2 also can be produced by well-known chemical synthesis techniques.

The four synthetic DNA oligomers are ligated to the IL-2 DNA to form a cointegrate fragment of approximately 730 base pairs (bp) in a 20 microliter reaction volume composed of 1 ul of each of the four synthetic DNA oligomers (20 nanograms (ng) each) with 5 ul of the IL-2 DNA fragments (200 ng). Also added are 2 ul of T4 DNA ligase and 2 ul 10×ligase buffer (0.66M Tris [pH 7.5], 50 mM magnesium chloride). Additionally added are 2 ul of 15 mM spermidine, 2 ul of 50 mM dithiothreitol, 2 ul of 1 mg/ml BSA and 1 ul of 20 mM adenosine triphosphate (ATP). The reaction is carried out by incubation overnight at 4° C.

The ligase mixture is electrophoresed on 1.2% agarose gel at 100 volts at room temperature. The region of the gel containing the 730 bp DNA fragments is excised and electroeluted from the gel. The DNA is extracted once with phenol:chloroform:isoamyl alcohol (25:25:1 volume). To the aqueouse phase, 2.5 volumes of 100% ethanol is added to precipitate the DNA. The solution is stored overnight at −20° C. and then centrifuged for 5 minutes at 10,000×g at room temperature, resulting in a pellet of the desired DNA product.

This 730 bp fragment has complementary ends that ligate to Hind III sites on the cloning vehicle plasmid.

The plasmid pYEJ001 (obtained from P. L. Biochemicals), as shown in FIG. 1, is prepared for ligation to the

TABLE 1

```
(1)                                              (2)
    A G C T G G C G G T G A T A A T G G T T G C A T G T A C T A A G G A G G T
            (3)
                    C C G C C A C T A T T A C C A A C G T A C A T G A T T C C T C C A

G T A T A T G G A C T A C A A A G A C G A T G A C G A C A A A G C A
(4)
        C A T A T A C C T G A T G T T T C T G C T A C T G C T G T T T C G T
```

The four oligomers in combination compose a translation initiation codon (ATG), bases coding for a ribosome binding site composed of the amino acid sequence and codons for the identification peptide defined by the amino acid sequence: Asp-Tyr-Lys-Asp-Asp-Asp-Asp-Lys. In the identification peptide, the sequence Asp-Tr-Lys constitutes the antigenic portion of the peptide while the sequence Asp-Asp-Asp-Asp-Lys constitutes the protease cleavable linking portion of the identification above prepared 730 bp fragment by digestion of the plasmid with Hind III restriction endonuclease, using 1 unit (U) of Hind III endonuclease per ug of DNA. The reaction includes 450 microliters of 1×Hind III buffer (70 mM Tris, [pH 7.4], 70 mM magnesium chloride, 0.6M NaCl). This mixture is incubated at 37° C. for one hour.

The linearized DNA is then phosphatased to prevent self-ligation with 45 ul of 10×CIP buffer (0.5M Tris

[pH 9.0], 10 mM magnesium chloride, 1 mM zinc chloride, 10 mM spermidine) and 1 ul of calf intestinal phosphatase (30 U). The mixture is incubated at 37° C. for 30 minutes and then extracted once with phenol:chloroform:isoamyl alcohol (25:25:1, vol.) as above. To the aqueouse phase 2.5 volumes (relative to the aqueous phase) of 100% ethanol are added and the resulting mixture is stored at −20° C. overnight. The mixture is then centrifuged at 10,000×g for 5 minutes at 22° C., yielding a pellet. The pelleted DNA is electrophoresed on a 0.7% agarose gel at 100 volts at 22° C. for 2 hours.

Digestion of plasmid pYEJ001 produces two DNA fragments, one of 3,273 bp and one of 787 bp. The larger fragment, as shown in FIG. 1, containing sequences encoding the tetracycline and ampicillin phenotypic markers, a lac operator and synthetic promoter, is isolated by electroelution and then extracted once with phenol:chloroform:isoamyl alcohol (25:25:1, vol.). To the aqueous phase are added 2.5 volumes of 100% ethanol and then the solution is stored at −20° C. overnight. The mixture is next centrifuged at 10,000×g for 5 minutes at 22° C. and the desired product is contained in the pellet.

The previously ligated identification peptide oligomers/IL-2 fragment is ligated to the above isolated 3,273 bp fragment of the pYEJ 001 plasmid by combining 2 microliters of the pYEJ001 3273 bp fragment (100 ng) with 500 ul of the combined identification peptide/IL-2 fragment (660 bp) prepared above, (100 nanogram) together with 2 ul of 10×ligase buffer (0.66M Tris [pH 7.5], 50 mM magnesium chloride), 2 ul of 50 mM dithiothreitol, 2 ul of 50 mM spermidine, 2 microliters of 1 mg/ml BSA, 1 ul of 20 mM adenosine triphosphate, 3 ul H$_2$O and 1 ul of T4 DNA ligase. The mixture is incubated at 15° C. overnight.

The resulting recombinant plasmid, designated as pImcf 001, is then transformed into *E. coli* strain RR1 using standard transformation techniques, such as disclosed in Maniatis et al, *Molecular Cloning: A Laboratory Manual*, Cold Spring Harbor Laboratory (1982). The host cells are grown in culture and then lysed. Plasmids from the host cells that have undergone transformation are checked for correct orientation of the foreign genes (cointegrate identification peptide oligomers/IL-2 fragment) within the plasmid.

EXAMPLE 2

Preparation of Plasmid for Yeast Host Cell Transformation

DNA fragments (660 bp) coding for IL-2 are prepared as described above in Example 1. Two synthetic DNA oligomers of 34 and 30 bases, as shown in Table 2, are chemically synthesized using standard techniques. As shown in the Table, one terminus of the synthetic DNA oligomers corresponds to an Eco RI cleavage site for subsequent ligation to a yeast plasmid, while the opposite end of the duplexed oligomers coincidentally corresponds to the Hae III cleavage site for subsequent ligation to the IL-2 DNA fragment. The synthetic oligomers, when duplexed, as shown in Table 2, code for the same identification peptide as in Example 1, but without a promoter site or a ribosome binding site.

The procedure for preparing a plasmid of the present invention for transformation of yeast host cells is shown in FIG. 2. The cloning vector, plasmid p219 is digested to completion with the restriction endonuclease Eco R1 by mixing 50 microliters of the plasmid (50 micrograms) with 450 microliters of 1×Hind III buffer and 10 microliters of Eco R1 restriction endonuclease. This mixture is incubated at 37° C. for 2 hours. The mixture is then heated to 65° C. for 10 minutes to inactivate the Eco RI enzyme. Thereafter, the plasmid is digested with Hind III under conditions of limiting enzyme. To this end, 2 ul of Hind III restriction endonuclease (10 U/ul) is added to the above mixture and then the mixture incubated at 37° C. for 20 minutes. The mixture is then heated to 65° for 10 minutes. The desired 7.4 kb fragment from the double digestion of the p219 plasmid is isolated by electrophoresis from an agarose gel as set forth above in Example 1.

As shown in FIG. 2, the synthetic DNA oligomers, the IL-2 DNA fragments and the desired linearized p219 vector fragment are ligated together in a reaction mixture composed of 1 ul of each of the two synthetic DNA oligomers (20 ng each) and 1 ul of IL-2 fragments (660 bp) (200 ng) and 1 ul (40 ng) of the 7.4 kb p219 plasmid in the presence of 1 unit of T4 DNA ligase and 2 ul of 10×ligase buffer (0.66M Tris [pH 7.5], 50 mM magnesium chloride). To facilitate ligation, 2 ul of 15 mM spermidine, 2 ul of 50 mM dithiothreitol, 2 ul of 1 mg/ml BSA, 1 ul of 20 mM ATP and 6 ul of H$_2$O are added resulting in a reaction volume of 20 ul. The reaction is carried out by incubation at 14° C. overnight.

The mixture thus composed is used directly to transform *E. coli* RR1. After the transformation process, the recombinant plasmid DNA, designated as pImyf 100, is isolated from the *E. coli* host and digested with several restriction endonucleases separately and in combination to determine that the correct plasmid has been constructed.

The recombinant DNA plasmid, pImyf 100, is employed to transform the DB746 strain of the Saccharomyces cerevisiae yeast. Prior to transformation, the DB746 strain is grown in culture in YP-glucose (200 milliliter) medium of 2×10$^7$ cells/ml. The cells are harvested by a centrifugation at 1,000×g for 5 minutes at 22° C. The pellet was washed with sterile distilled water.

The yeast cells were then concentrated by resuspending in 20 milliliters of SED (1M sorbitol, 25 mM EDTA [pH 8.0], and 50 mM dithiothreitol) and incubated for 10 minutes at 30° C. The cell-buffer mixture is then centrifuged for 5 minutes at 300×g. The pellet is washed once with 200 milliliters of 1M sorbitol and the cells resuspended in 20 milliliters of SCE (1M sorbitol, 0.1M sodium citrate [pH 5.8]=0.01M EDTA). Glusulase, to break down the cell walls, in an amount of 0.2 ml is added to the solution and then the solution incubated at 30° C. for 30 minutes with occasional gentle shaking.

The presence of spheroplasts is assayed by diluting 10 microliters of the yeast cells into a drop of 5% sodium dodecyl sulfate (SDS) (wt./vol.) on a microscope slide to observe for "ghosts" at 400×phase contrast.

The cell mixture is then centrifuged at 300×g for 3 minutes. The resulting pellet is twice washed with 20 ml

TABLE 2

A A T T A T G G A C T A C C C G G A C G A C G A G G A C A A G G C C
T A C C T G A T G T T C C T G C T G C T C C T G T T C C G G of 1M sorbitol. The pellet is then once washed in STC (1M sorbitol, 10 mM CaCl, 10 mM Tris HCl [pH 7.5]).

The yeast spheroplasts are then transformed with the previously prepared plasmid vector in a procedure adapted from Beggs, supra. The pelleted protoplasts are suspended in 1.0 milliliters of STC and then divided into 100 microliter aliquotes in 10 ml disposable tubes (Falcon #2059). Then, from 1 to 10 ul of the DNA plasmids are added to each aliquot (0.5 to 5 ug). The mixture rests at room temperature for 10 minutes and then 1 ml of PEG (20% PEG 4000, 10 mM CaCl$_2$, 10 mM Tris-HCl [pH 7.4]) is added to each aliquot to promote DNA uptake. After 10 minutes at room temperature, the mixture is centrifuged for 5 minutes at 350×g. The resulting pellet is resuspended in 150 ul of SOS (10 ml of 2M sorbitol, 6.7 ml of YEP, 0.13 ml of 1M CaCl$_2$, 27 ul of 1% lycine, and 3.7 ml of water). This mixture is incubated for 20 minutes at 30° C. The cells are then plated, or held at 4° C. for up to a few days.

Prior to plating the protoplast/DNA mixture, plates are preincubated at 37° C. and then TOP agar is added and then the plates held at 45° C. TOP agar is composed of 18.2 ml of sorbitol, 2 gm agar, 0.6 gm Difco yeast nitrogen base (without amino acids), 2 gm glucose, 0.1 ml of 1% adenine, 0.4 ml of 1% uracil and amino acids, as required). Six ml of TOP agar is then added to each aliquot and then the tube contents poured on the plated agar. The plates are incubated from 2 to 4 days at 30° C. Colonies which develop in the Trp minus medium contain plasmids that have the Trp 1 gene, i.e., those that are transformed.

EXAMPLE 3

Biochemical Synthesis of Di-Palmityl Derivatized Identification Peptide

Solid phase chemical synthesis is used to prepare a di-palmityl derivitized identification peptide having the following composition:

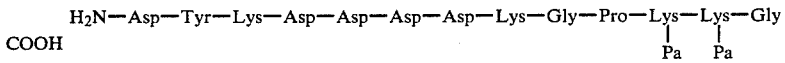
COOH

The synthesis of the identification peptide commences from the carboxyl terminal (COOH) residue. In the synthesis process, 0.5 gm of N-alpha-butyloxycarbonyl (alpha-BOC) Gly resin (Peninsula Labs) is washed two times with 10 ml of the solvent methylene chloride (CH$_2$Cl$_2$, Baker Laboratories). The resin is then washed once with 10 ml of 30% v/v Trifluoroacetic acid (TFA, Pierce Biochemicals) in CH$_2$Cl$_2$.

The alpha-BOC group is removed from the Gly by reacting the resin with 10 ml of 30% (v/v) TFA in CH$_2$Cl$_2$. The mixture is shaken for 30 minutes at room temperature. The resin is then washed 3 times with 10 ml CH$_2$Cl$_2$.

Deprotection of the resin is confirmed by a Ninhydrin (color) test on a small sample of the resin. 1 mg of resin is placed in a 10×75 mm glass tube. To the tube are added: 3 drops of 80% phenol diluted in ethanol (v/v); 3 drops of pyridine; and, 3 drops of 5% Ninhydrin diluted in ethanol (w/v). The mixture is boiled for 5 minutes. If the resin turns dark blue, it has been "deprotected," if it does not the above procedure is repeated.

The resin is then neutralized by adding 10 ml of the hindered base with 5% (v/v) di-isopropyl ethylamine (redistilled DIEA, Aldrich Chemicals) diluted in CH$_2$Cl$_2$ (v/v), and shaken at room temperature for 5 minutes. The fluid is decanted and this step repeated. The resin is then washed again three times in 10 ml CH$_2$Cl$_2$.

The diamino acid Lys in the derivative form alpha-butyloxycarbonyl-epsilon-fluoreylmethyloxycarbonyl (alpha-BOC-epsilon FMOC) is activated for subsequent bonding to the deblocked Gly resin by mixing 2 millimoles (mM) of Lys derivative with 1 mM of the carbodiimide condensing agent dicyclohexylcarbodiimide (DCC, Sigma) dissolved in 10 ml CH$_2$Cl$_2$. This mixture is reacted for 10 minutes on ice then filtered. The filtrate consisting of activated alpha-BOC-epsilon-FMOC-Lys is added to the resin and shaken for 2 hours at room temperature. The resin is then washed two times in 10 ml CH$_2$Cl$_2$.

The ninhydrin test, as described above, is then repeated to determine if coupling has occurred, i.e., whether the resin remains yellow. If instead the resin turns purple, indicating an incomplete reaction, the coupling procedure described above beginning with the neutralization of the resin with DIEA is repeated in modified form. Ten ml of 5% DIEA in CH$_2$Cl$_2$ (v/v) is added to the resin and then the mixture is shaken for 5 minutes at room temperature. The resin is washed 3 times with 10 ml CH$_2$Cl$_2$. Next, 1.26 mM of DCC, 2 mM of hydroxybenzotriazole (HOBT, Aldrich) (as an alternative to the use of DCC above) and 1.27 mM alpha-BOC-epsilon-FMOC-Lys are dissolved in 10 ml of dimethylformamide (DMF, Pierce) (as an alternative solvant to CH$_2$Cl$_2$) and allowed to react for 10 minutes at 0° C. This mixture, containing the active amino acid HOBT ester, is added to the deprotected resin and shaken for 4 hours at room temperature to complete the coupling reaction. The resin is then washed twice with 10 ml DMF, and then twice with 10 ml CH$_2$Cl$_2$. The ninhydrin test is repeated. If the resin remains yellow (negative), it is ready for binding of palmitic acid.

The addition of palmitic acid to the Lys residue, which has been linked to the Gly-coupled resin, is accomplished by repeating the above procedure in modified form. An initial washing of the resin with CH$_2$Cl$_2$, is followed with a washing with 10 ml of 50% piperidine in CH$_2$Cl$_2$ (v/v) (instead of TFA). Next, the epsilon amino group of the FMOC-Lys is deprotected by adding 10 ml of 50% piperidine (diluted in CH$_2$Cl$_2$) and shaken at room temperature for 30 minutes. The mixture is next washed three times with 10 ml CH$_2$Cl$_2$.

Two mM of palmitic acid is reacted with the epsilon amino group by the same procedure used to couple the alpha-BOC-epsilon-FMOC-Lys. This procedure thus yields a palmityl-derivatized amino acid coupled to the preceding amino acid (Gly which is attached to the resin) to facilitate micelle formation for immunization.

The identification peptide synthesis continues with addition of a second palmityl-derivatized amino acid residue (Lys) by repeating the above procedures. Thereafter, the remainder of the amino acid residues constituting the derivatized peptide are added by substituting the appropriate amino acid for the Lys residue used above to the desired length of the identification peptide. After coupling of the final Asp residue, the N-terminus of this residue is deprotected by washing the resin twice in $CH_2Cl_2$ and then once in 10 ml of 30% TFA (v/v in $CH_2Cl_2$). Next, 10 additional ml of 30% TFA (v/v in $CH_2Cl_2$) is added to the resin and the mixture shaken for 30 minutes at room temperature. Later the resin is washed three times in $CH_2Cl_2$.

After completion of the coupling procedure described above, the entire palmityl-derivatized peptide molecule is cleaved from the resin and the side blocking groups of the residues are deprotected using hydrogenfluoride (HF) to yield a sequence of amino acids with two lysine residues derivatized with palmitic acid. Deprotection of the side groups and cleavage is accomplished by placing the peptide molecule in a reaction flask to which a dry stir bar is added. 1.0 ml of anisole (Aldrich) is added to the flask to protect the Tyr residue. The flask is cooled for 10 minutes on dry ice/methanol. The mixture is subjected to a vacuum with an aspirator for several minutes to 340 mm Hg. Then a hydrogenfluoride (HF) source is connected to the flask to cleave the completed peptide from the resin bead and simultaneously remove the side-chain protecting groups from the peptide. HF is condensed into the reaction flask to the 10 ml mark.

The mixture in the flask is then stirred in an ice water bath for 30 minutes for standard Merrifield resin or 60 minutes for benzhydrylamine resin and 45 minutes if sensitive amino acids are present. The flask is slowly subjected to a vacuum while continuing to stir in the ice water bath. The flask is kept under vacuum until the resin is completely dry.

The resin is washed 2 times with 10 ml of petroleum ether. 10 ml of glacial acetic acid (HAc) is added and the mixture is stirred and then allowed to sit for 10 minutes. The resin thereafter is warmed at 55° C. for 2 minutes. Next, the resin/HAc is poured into a 15 ml coarse frit Buchner funnel on a 50 ml filter flask. The resin is washed with 10 ml HAc. The HAc filtrates are transferred to a 50 ml polypropylene centrifuge tube and lyophilized overnight. The resulting product is di-palmityl derivatized identification peptide which can be used to raise antibodies against the antigenic portion of the peptide. Prior to such use, the identification peptide is dialysed against water or PBS with a molecular weight cutoff from 6 to 8 thousand daltons.

EXAMPLE 4

Production of Monoclonal Antibody

BALB/c mice were initially immunized subcutaneously in the right and left hind legs with 100 ug of di-palmityl derivitzed identification peptide, for instance, from Example 3 above. Prior to immunization, the identification peptide was prepared as an emulsion by mixing 4 mg of the identification peptide in 2 ml of double distilled sterile water and then adding 2 ml of complete Freund's adjuvant (Difco Laboratories, Detroit, Mich.). After the initial immunization, the mice were rechallenged bi-monthly with 100 mg of di-palmityl derivitized identification peptide in incomplete Freund's adjuvant.

After the second immunization and each immunization thereafter, the animals were bled retro-orbitally with a sterile pipet. The collected blood as allowed to clot for the 30 minutes at room temperature and then the serum prepared by centrifugation of the clotted blood for 10 minutes at $450 \times g$. This serum was tested for anti-identification peptide antibody response by use of ELISA assay, as detailed previously. The ELISA assays were repeated after each subsequent immunization until mice were identified which produced significant serum titer against the identification peptide. Once a high serum titer was detected, the animals were given an intravenous injection of di-palmityl derivitized identification peptide in saline.

Three to four days later the animals were sacrificed by cervical dislocation. The spleens from these animals were harvested and single cell suspensions prepared therefrom. The spleens were cultured in Click's medium (Altick Associates, Hudson, Wis.). The medium was supplemented with 10% (vol./vol.), heat-inactivated fetal calf serum (FCS), 300 ug/ml of fresh L-glutamine, 50 ug/ml of gentamycin, 50 U/ml of penicillin, 50 ug/ml of streptomycin, 25 mM Hepes buffer and 16 mM $NaHCO_3$ (complete Click's medium).

Fusion was achieved by mixing approximately $20 \times 10^6$ spleen cells with approximately $10 \times 10^6$ NS1 murine myeloma cells in a 15 ml conical centrifuge tube. The cell mixture was pelleted by centrifugation for 10 minutes and $250 \times g$ and the supernate discarded. One ml of a solution of 40 percent (weight/volume) of PEG diluted in complete Click's medium was then added to the cell pellet in dropwise manner. Thereafter, 10 ml. of complete Click's medium was added to the centrifuge tube over a 2 minute period and the cell pellet gently resuspended. Next, the mixture was centrifuged for 5 minutes at $250 \times g$ and the supernate discarded to complete the fusion process.

Anti-identification peptide antibody was derived from the fused cells designated as 7C8, by resuspending the resulting cell pellet in 40 ml of complete Click's medium. The unfused myeloma driver cells (NS1), double NS1 hybrids, unfused spleen cells and double spleen cell hybrids were prevented from proliferating by the addition to the medium of approximately 1.36 mg/ml of hypoxanthene, 0.00176 mg/ml of aminopterin and 0.388 mg/ml of thymidine (complete Click's HAT medium). Also, approximately $120 \times 10^6$ BALB/c mice thymidine cells were added as filler cells. The entire cell suspension was then divided into 200 microliter aliquots in flat-bottom microtiter plates (No. 3596 Costar Inc., Cambridge, MA). The cultures were all maintained at approximately 37° in a humidified atmosphere of 7% $CO_2$ in air. After from 7 to 10 days of culture, supernates from wells containing viable hybrid cells were tested by ELISA for the presence of anti-identification peptide antibody.

The 7C8 cell line was found to produce antibody having a low affinity to the identification peptide and thus would be useful in the purification of the hybride identification peptide/protein molecule, as discussed above. Samples of this cell line are on deposit with the ATCC under accession number HB 8465.

EXAMPLE 5

In Vivo Production of Hybridoma Cells Producing Monoclonal Anti-Identification Peptide Antibodies Anti-identification peptide antibody was produced in high concentration in vivo by intraperitoneal injection of BALB/c mice with approximately $2 \times 10^6$ hybridoma cells. One week prior to hybridoma cell injection, recipient BALB/c mice were given 1.0 ml of pristane intraperitoneally as an ascites inducing irritant. From 8 to 14 days after hybridoma injection, intraperitoneal ascites were collected and then the hybridoma cells in the fluid pelleted by centrifuging for 10 minutes at $1000 \times g$. The resulting supernate was found to contain monoclonal anti-identification peptide antibody at concentrations in excess of 3 ug/ml.

EXAMPLE 6

Affinity Chromatography Purification of Hybrid Identification Peptide/Protein Molecules Monoclonal anti-identification peptide antibodies (produced as described above) were selected for affinity purification by the ability of free identification peptide to inhibit the antibodies from binding to identification peptide-coated microtitre plate wells in ELISA assays. An antibody with a low affinity to the identification peptide was chosen for use on the affinity matrix column.

In the affinity chromatography procedure, purified antibody is dialyzed against 1000 volumes of BBS (50 mM borate, 150 mM NaCl [pH 8.5]) and then coupled to Affi Gel 10 (Biorad Laboratories) by overnight incubation at 4° C. according to the instructions supplied with the Affi Gel. Unreacted sites on the Affi Gel are then blocked by addition of from 10 to 100 mM glycine ethyl ester. The antibody-coupled gel, containing approximately 2 mg of antibody/ml of gel, was washed extensively with 1N PBS.

The hybrid identification peptide/protein molecules were then applied to the gel column at a rate of 1.0 ml/minute at 4° C. The column was washed with PBS. The flow to the column is then reversed and specific elution of the hybrid identification peptide protein molecules was achieved by pumping through a 1N PBS solution containing 0.5M of synthesized free identification peptide to displace the hybrid molecules from the column.

EXAMPLE 7

Cleavage of the Purified Identification Peptide Protein Hybrid Using Sequence-Specific Proteolytic Enzyme Affinity chromatography purified hybrid peptide protein, obtained from Example 6 above, is suspended in from 1 to 100 ml of Tris buffer [pH 8.0]) at concentrations of 0.1–5 mg/ml of protein. Bovine mucosal enterokinase is added to the suspension to yield a final concentration of 100 to 50,000 U/ml of protease activity (Units defined by Liepnicks and Light, 254 General Biochemistry 1677 (1979)). The suspension is then incubated at room temperature for 8–72 hours.

After incubation, the suspension is treated to obtain pure protein product by raising the ionic strength of the suspension by addition from 1 to 100 ml of 0.5M NaCl while keeping the pH at 8.0. Following this adjustment, the suspension is passed over an affinity column containing immobilized pancreatic trypsinogen, the natural substrate for bovine mucosal enterokinase. The enterokinase is thereby bound to the column and the desired protein product passes through the column.

The flow-through from the column is next passed over an affinity column which contains immobilized anti-identification peptide antibody. The cleaved identification peptide will bind to the column along with any residual uncleaved hybrid identification peptide/-proteins. The eluate from the column contains only pure mature protein product.

As will be apparent to those skilled in the art to which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples set forth in the foregoing description.

The embodiments of the invention in which an exclusive property or privilege is claimed are defined as follows:

1. A DNA expression vector comprising DNA coding for a hybrid polypeptide comprising
   (1) an identification peptide consisting of a hydrophilic antigenic N-terminal sequence of up to six amino acids comprising both hydrophilic and aromatic amino acids and including the sequence Asp-Tyr-Lys;
   (2) a constituent polypeptide; and
   (3) a linking sequence of amino acids interposed between the identification peptide and the constituent polypeptide, said sequence being cleavable by a sequence-specific proteolytic agent at a specific amino acid residue adjacent to the constituent polypeptide.

2. A vector according to claim 1, wherein the antigenic sequence comprises a plurality of amino acids of the group consisting of Arg, Asp, Glu, Lys, Tyr, Phe, His and Trp.

3. A vector according to claim 2, wherein the linking sequence is Asp-Asp-Asp-Asp-Lys.

4. A DNA expression vector comprising DNA coding for a hybrid polypeptide comprising
   (1) an identification peptide consisting of the amino acid sequence Asp-Tyr-Lys-Asp-Asp-Asp-Asp-Lys; and
   (2) a constituent polypeptide.

5. A method for producing a selected protein molecule, comprising:
   a. producing a DNA expression vector comprising DNA coding for a hybrid polypeptide comprising
      (1) an identification peptide consisting of a hydrophilic antigenic N-terminal sequence of up to six amino acids comprising both hydrophilic and aromatic amino acids and including the sequence Asp-Tyr-Lys;
      (2) a constituent polypeptide; and
      (3) a linking sequence of amino acids interposed between the identification peptide and the constituent polypeptide, said sequence being cleavable by a sequence-specific proteolytic agent at a specific amino acid residue adjacent to the constituent polypeptide;
   b. transforming host cells with said expression vector; and
   c. isolating said selected protein by removing said polypeptide from said transformed cells and purifying the polypeptide by use of the ligand affinity properties of the identification peptide.

6. A method for producing a selected protein molecule, comprising:
   a. producing a DNA expression vector comprising DNA coding for a hybrid polypeptide comprising
      (1) an identification peptide and linking sequence consisting of the amino acid sequence Asp-Tyr-Lys-Asp-Asp-Asp-Asp-Lys; and
      (2) a constituent polypeptide;
   b. transforming host cells with said expression vector; and
   c. isolating said selected protein by removing said polypeptide from said transformed cells and purifying the polypeptide by use of the ligand affinity properties of the identification peptide.

* * * * *